(12) United States Patent
Sjaunja

(10) Patent No.: US 7,229,830 B1
(45) Date of Patent: Jun. 12, 2007

(54) STANDARD SAMPLE COMPOSITION AND MANUFACTURE THEREOF

(76) Inventor: Lars-Ove Sjaunja, Fibyvagen 3, Vange (SE) S-740 20

( * ) Notice: Subject to any disclaimer, the term of this patent is extended or adjusted under 35 U.S.C. 154(b) by 1034 days.

(21) Appl. No.: 10/130,713

(22) PCT Filed: Nov. 23, 2000

(86) PCT No.: PCT/SE00/02305

§ 371 (c)(1),
(2), (4) Date: Aug. 22, 2002

(87) PCT Pub. No.: WO01/38868

PCT Pub. Date: May 31, 2001

(30) Foreign Application Priority Data

Nov. 23, 1999 (SE) .................................... 9904229

(51) Int. Cl.
*G01N 31/00* (2006.01)
(52) U.S. Cl. ............................. 436/8; 436/19; 436/20; 436/21; 436/174
(58) Field of Classification Search .................... 436/8, 436/19, 20, 21, 22, 23, 174
See application file for complete search history.

(56) References Cited

U.S. PATENT DOCUMENTS

| 3,573,062 A | 3/1971 | Paynter et al. |
| H35 H * | 3/1986 | Berkowitz .................. 426/135 |

FOREIGN PATENT DOCUMENTS

| EP | 0 962 768 A2 | 12/1999 |
| WO | WO 81/02467 | 9/1981 |

OTHER PUBLICATIONS

W. Ooghe et al., "Comparison of Some Additivies Used in the Preparation of Freeze-Dried Lemon Juice Candidate Reference Materials," *Fresenius' J. Anal. Chem.*, V. 360(3-4), 1998, abstract.

* cited by examiner

*Primary Examiner*—Maureen M. Wallenhorst
(74) *Attorney, Agent, or Firm*—Young & Thompson

(57) ABSTRACT

A standard sample composition containing a complexing agent and an alkali salt, mixed with a known amount of a foodstuff, the content of at least one component of which is accurately known. The mixture is dissolved in a solvent, e.g. water, and comminuted to form a dispersion. The solvent is removed e.g. by freeze-drying or other suitable method, such that the water content of the composition is <5% by weight, preferably <1% by weight, more preferably <0.1%, most preferably <0.01% by weight of the total composition.

20 Claims, 1 Drawing Sheet

STANDARD SAMPLE COMPOSITION AND MANUFACTURE THEREOF

The present invention relates to analysis of foodstuff and/or feedstuff in general, and in particular to a composition for a standard sample suitable for the calibration of analysis equipment.

BACKGROUND OF THE INVENTION

In my own European Patent Application EP 0 962 768 (corresponding to Swedish patent application SE-9801827-8), incorporated herein in its entirety by reference, there is disclosed and claimed a product suitable for dispersing foodstuff for analytical purposes. The object of the invention claimed therein is to prepare samples that are possible to analyze with as few errors and artifacts in the analysis results as possible.

The product claimed in EP 0 962 768 comprises a composition of a complexing agent, e.g. emulsifying salts and an alkali salt. The product is dissolved in water and the foodstuff to be analyzed is mixed with the solution, and the mixture is milled in a suitable mill. A homogeneous dispersion in liquid form results, having a milk-like appearance. This dispersion is then readily analyzed by common methods, such as mid-infrared (MIR) spectroscopy, UV spectroscopy or chemical extraction methods, to mention some.

A problem in all analyses of complex compounds or material is to be sure that the analytical results are accurate. The accuracy and precision of different analysis methods have to be validated frequently with (standard) reference samples and/or in collaborative studies. For inorganic compounds there are standard samples available. For organic compounds like fat, protein, carbohydrate in different foodstuffs, long-life standard samples are not so common as in general, it is more complicated to store the foodstuffs or samples without any deterioration of the different compounds. In the food industry for analytical purposes the validation of different methods are mainly controlled and calibrated by analysing the control or calibration samples with the routine method as well as with some reference chemical methods. The chemical methods are often time-consuming and complicated and therefore expensive. In most cases the samples are sent to a reference laboratory. It can take some days or weeks to obtain an answer, but usually the routine laboratory needs the results immediately.

Therefore, there is a great demand of long-life standard samples of different foodstuffs in the food and feed laboratories, so the different methods can be controlled and calibrated immediately.

SUMMARY OF THE INVENTION

Thus, there is a need for a reliable standard sample, having a guaranteed long term stability, at least of the order of 1–12 months, preferably 24 months or more, which is easily dissolved, preferably instantly, in the medium used, commonly water, but also in other polar solvents e.g. di-methyl-sulphoxide (DMSO), and which enables an analysis of a complex material such as a foodstuff/feedstuff to be performed much faster than today.

The object of the invention is therefore in a first aspect to provide a standard sample composition having the above mentioned properties. This is achieved by the composition defined in claim 1, which essentially is a dry powder comprising a foodstuff (or feedstuff) of interest. Important is that the water content of the foodstuff in native state is known. Preferably a well defined amount of said foodstuff itself is comprised. Also it has preferably known values of the content of specific substances of interest, e.g. fat, proteins, carbohydrates etc.

In a preferred embodiment the water content of the sample composition is <5% by weight of water on the basis of the total composition, preferably <1% by weight, more preferably <0,1% by weight, most preferably <0,01% by weight of the total composition.

Suitably the powder is a freeze-dried powder.

In an alternative embodiment the standard sample composition is a frozen suspension of the components in the powder product of claim 1.

In a second aspect there is provided a method of manufacturing a standard sample composition, and such a method according to the invention is defined in claim 9.

Finally, there is also provided a method of analysis employing the standard sample composition as defined in claim 1. This analysis method is defined in claim 11.

BRIEF DESCRIPTION OF THE DRAWING

The invention will now be described in further detail with reference to examples and the drawing, in which the only FIGURE (FIG. 1) shows the correlation between a reference chemical method and an IR method using the invention.

DETAILED DESCRIPTION OF THE INVENTION

Figure 1:
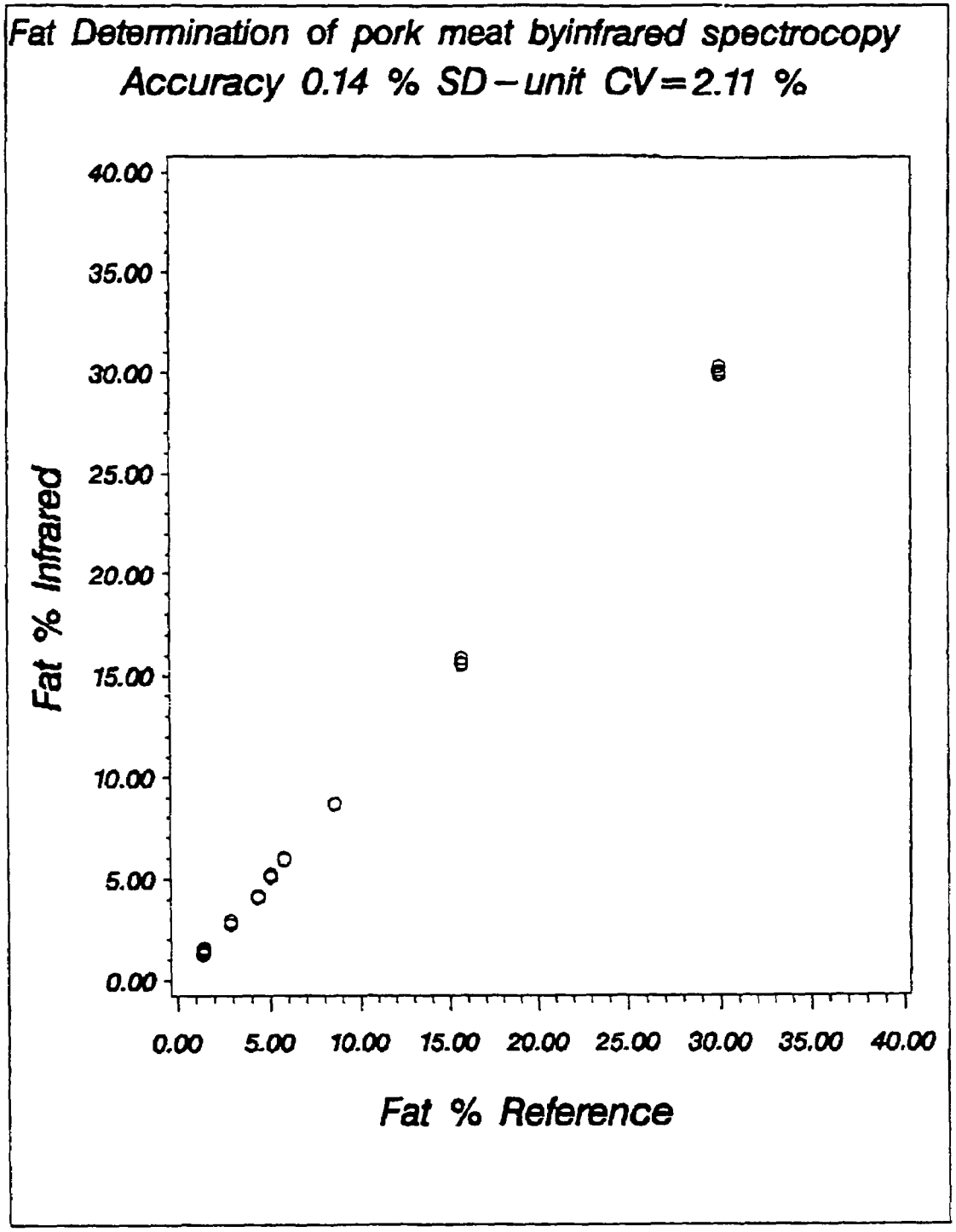

The invention will be described with reference to the method of manufacturing, and the product will be exemplified by examples of analysis of various types of foodstuff. For the purposes of this application, the term "foodstuff" shall be taken to include foodstuff (for human beings) and feedstuff or fodder (for animals).

By "precursor" as used herein, we mean an intermediate product that is to be finally treated to arrive at the claimed formulation.

By the term "native state" we mean the state of a foodstuff in which an analysis is to be performed thereon. Thus, it can be both raw or cooked meat, fresh or pasteurized milk, etc.

Thus, a precursor of the standard sample composition according to the invention is made by essentially the same method as disclosed in the above referenced EP 0 962 768. Namely, a combination of a complexing agent and an alkali salt is made by mixing the components in suitable proportions. The mixture is dissolved in water, and then a quantity of the foodstuff of interest, suitably cut in pieces, is added to the solution. Preferably a composition as disclosed in EP 0 962 768 is used. It comprises as a complexing agent sodium citrate or one or more phosphates from the group consisting of sodium citrate, sodium di-hydrogenphosphate, di-sodium hydrogenphosphate, di-sodium di-hydrogen pyrophosphate, tri-sodium monohydrogen pyrophosphate, tetra-sodium pyrophosphate, penta-sodium triphosphate and sodium hexametaphosphate, phosphonic acids, NTA, EDTA, zeolites, e.g. Na—Al-silcate, and polycarboxylates, or combinations thereof. As the alkali the composition comprises one or more substances selected from the group consisting of sodium or potassium soda ($Na_2CO_3$, $K_2CO_3$), silicates e.g. sodium or potassium meta-silicate and optionally a hydroxide, e.g. sodium or potassium hydroxide.

It is important that the water content of the foodstuff in question in the native state, as defined above, is accurately known. This is because one has to know exactly how much water needs to be added to the product standard sample powder to bring it back into dispersion, such that the concentration of the component of interest will be the expected in a reproducible way.

In a first embodiment, the foodstuff will have a known composition also in terms of the component thereof that is of interest for the analysis, in addition to that of water. I.e. if the purpose is to prepare a standard sample for fat content in cheese, the fat content of the cheese to be used for the manufacture of the standard sample should be accurately known, by other analysis, e.g. by methods approved by AOAC, ISO or IDF. In principle any component of any foodstuff could be used as the basis for the standard sample, as long as it is possible to obtain an accurate analysis of the raw material, in respect of the component substance of interest.

When the foodstuff has been put into the solution, the mixture is treated in a mill in order to comminute the pieces of the foodstuff, such that a dispersion or suspension is formed.

Suitably a special mill manufactured by L O Sjaunja AB, Uppsala, Sweden can be used. It is available under the trade name LOSMIXER.

Of course other mixers/mills may be used as long as they produce a sufficiently fine comminution of the foodstuff. The criterion that the mill must meet is that it should be able to produce a fine dispersion with microparticles, where most of the dispersions are in a colloidal phase, or that the sedimentation rate is less than some mm per hour. In the case of fat, the fat must be in a homogenous emulsion insuring that fat does not separate out, giving a fat layer on the surface. Separated fat implies that it is difficult to take out a representative sample.

The grounding in the mill is performed during a time period of about 20–300 seconds, and the result is a dispersion (suspension) having mostly a milk-like appearance. The particle size is preferably in the colloidal range or at least most of the organic particles should be in that range. The average particle size should preferably be <50 µm, more preferably <10 µm, and most preferably <1 µm.

In a second embodiment the content in the foodstuff of the component or components of interest is not measured on the raw material but instead by analysis of the dispersion obtained by the milling operation.

Now there are two possible ways to obtain a standard sample that may be stored and transported. The dispersion as obtained from the milling process can be frozen, and supplied to the end user in vial containing an accurately measured quantity. This is entirely within the inventive concept, but has the drawback that it needs to be kept under deep-frozen conditions.

Thus, preferably the dispersion is subjected to a drying process in order to reduce the water content to <5% by weight, preferably to <1% by weight, more preferably to <0,1%, most preferably to <0,01% by weight.

This can be done by ambient pressure evaporation, vacuum evaporation, or freeze-drying, the latter being the preferred method.

Conventional apparatus and methods for drying, well known by the skilled man are usable, and will not be discussed further herein.

In a further embodiment of the invention, the content of the component in the standard sample can be determined on the final end product, i.e. the (freeze) dried material.

In a further aspect the invention comprises an analysis procedure, wherein analysis equipment is calibrated or checked for reproducibility by employing a standard sample of the invention. For calibration purposes the content in the standard sample of the component of interest must be accurately known, but for reproducibility purposes it suffices to know that the standard sample composition itself is constant over time, such that a stock sample always will give the same result.

The invention will now be further illustrated in detail by way of the following non-limiting examples that are given for illustration purposes only.

EXAMPLES

Example 1

A commercial matured cheese of the age of approx. 6 months was used in this experiment. The used cheese was gouda type cheese (Prästost). The composition of the cheese was 31% by weight (m/m) fat, 25.4% by weight(m/m) protein, 1.0% by weight lactic acid, 1.1% by weight sodium chloride (NaCl) and 39% by weight of water. A total amount of 500 g of cheese was used. Due to the mixing capacity the mixing was repeated 50 times. Each time 10 g cheese was mixed with 90 g of LOSsolver solution (manufactured by L O Sjaunja AB, Uppsala, Sweden) in 60 sec. in a LOSmixer (manufactured by L O Sjaunja AB, Uppsala, Sweden). The homogenous dispersion was then freeze-dried (at a condensator temp. of −50° C., and a vacuum pressure of 0.07 hPa) in a freeze-dryer (Heto CD8, manufactured by Heto Lab Equipment A/S, Birkeröd, Denmark) to a dry-matter content >99% by weight (m/m). The cheese powder was stored in chemical and thermal shock resistance bottles of Duran borosilicate glass. The samples were then stored in ambient temperature for 1.5 years. The cheese powder was easily dissolved in distilled water. The powder was instantly dissolved into a homogenous solution (dispersion), only by mixing the powder with a spoon or similar. By "instantly" is meant that a dispersion is obtained within say 10 seconds, preferably within 5 seconds. If some heating is performed, e.g. to 40° C., the dissolution will take place quicker. The solution was made up by taking 6.9 g of cheese powder and 93.1 g of distilled water. These amounts means that the original concentrations are prepared. The freeze dried cheese powder was than analyzed every month with infrared spectroscopy. The reproducibility between the determinations was excellent. The relative deviation was less than 1%, which means that the absolute deviation of the fat content was ±0.3%.

Example 2

Standard samples of meat were prepared in the same way as for cheese. A lean pig meat of the muscle m. longissimus dorsi was used in this preparation. The composition of the meat was 1.6% by weight fat, 23.1% by weight protein, 1.2% by weight ash and 74.2% by weight water. 10 g of meat was mixed and milled with 90 g of "LOSsolver meat" solution (manufactured by L O Sjaunja AB, Uppsala, Sweden) in a blender/mixer (LOSmixer, manufactured by L O Sjaunja AB, Uppsala, Sweden). The solution was heated to 40° C., before added to the mixer. The total mixing time was 2 minutes. The meat dispersion had a high degree of foaming. The foams were minimized by adding 100 µl of Antifoam A concentrate (manufactured by Sigma, Steinheim, Germany). The homogenous meat dispersion was then freeze dried in a freeze dryer to a dry-matter content >99% by weight. The meat powder was stored in the same manner as the cheese powder. The meat powder was analyzed on the preparation day and after 2 months, with the same result.

Although, the meat samples can be somewhat more difficult to bring to a dispersion than the cheese samples, also the meat sample can be said to dissolve "instantly" for the purposes of the invention. The reproducibility between the two analysis occasions was within 1% (relative). The meat standard samples are intended to be stored for at least 1 year.

Example 3

12 meat samples of 10–12 g meat and 108 g Of 40° C. LOSsolver Mea™ (L -O Sjaunja AB, Uppsala) were homogenized at 40° C. in a LOSmixer™ (L -O Sjaunja AB, Uppsala). Each meat sample was analyzed for fat content by independent chemical analysis as reference, and the contents are shown in Table 1 under heading "Fat %, Reference". After three minutes, 20 droplets of Antifoam B (Sigma Chemicals Co.) were added to each sample, and the solutions were mixed for another five seconds. Each solution was transferred into a beaker and left to stabilize for a few minutes. Finally filtration was carried out by using a 80 μm steel mesh.

A blank solution was prepared by mixing 90 ml LOSsolver Meat™, 10 ml of Milli-Q water and 20 droplets of Antifoam B. The pH was adjusted to 10.2 by adding appropriate amounts of concentrated HCl.

The instrument used, an infrared spectrometer, Dairylab 2 from Multispec Limited, which is a single-beam instrument designed for direct determinations of milk products, was zeroed against water and each sample was analyzed twice. The blank solution was analyzed before and after the samples to discover possible instrumental drift during measurements. All solutions were temperatured to 40° C. prior to analysis.

The results of the analyses compared with reference measurements are shown in Table 1.

TABLE 1

Fat determination of pork meat, dissolved in LOSsolver meat, with infrared spectroscopy and reference (chemical) method. Two analyses were made on each sample.

| Sample no | Fat % IR | Fat % Reference | Difference % IR-reference |
|---|---|---|---|
| 1 | 1.34 | 1.47 | −0.13 |
| 1 | 1.34 | 1.47 | −0.13 |
| 2 | 2.78 | 2.89 | −0.11 |
| 2 | 2.76 | 2.89 | −0.12 |
| 3 | 4.07 | 4.36 | −0.29 |
| 3 | 4.07 | 4.36 | −0.29 |
| 4 | 5.92 | 5.78 | 0.14 |
| 4 | 6.02 | 5.78 | 0.25 |
| 5 | 8.70 | 8.59 | 0.11 |
| 5 | 8.67 | 8.59 | 0.08 |
| 6 | 15.53 | 15.72 | −0.20 |
| 6 | 15.52 | 15.72 | −0.20 |
| 7 | 29.88 | 30.02 | −0.15 |
| 7 | 29.98 | 30.02 | −0.04 |
| 8 | 1.58 | 1.42 | 0.16 |
| 8 | 1.52 | 1.42 | 0.10 |
| 9 | 1.48 | 1.40 | 0.08 |
| 9 | 1.50 | 1.40 | 0.11 |
| 10 | 1.60 | 1.44 | 0.15 |
| 10 | 1.61 | 1.44 | 0.17 |
| 11 | 1.37 | 1.40 | −0.02 |
| 11 | 1.39 | 1.40 | −0.01 |
| 12 | 5.07 | 5.06 | 0.02 |
| 12 | 5.08 | 5.06 | 0.03 |

The excellent correlation between reference method and the IR method using the inventive composition is shown in the appended FIG. 1, the correlation value being 0,99.

Although the invention has been described with reference to cheese and meat, the skilled man will be able to implement the inventive idea for numerous other foodstuffs without inventive work, and the invention is thus limited only by the scope of the claims.

The invention claimed is:

1. A standard sample composition, comprising: a) a comminuted foodstuff, the water content of which in a native state is accurately known;
   b) a complexing agent selected from the group consisting of sodium acetate, sodium citrate, sodium di-hydrogenphosphate, di-sodium hydrogenphosphate, di-sodium di-hydrogen pyrophosphate, tri-sodium monohydrogen pyrophosphate, tetra-sodium pyrophosphate, penta-sodium triphosphate, sodium hexametaphosphate, phosphonic acids, NTA, EDTA, zeolites, Na—Al-silcate, polycarboxylates, and combinations thereof, and
   c) an alkali salt;
   and wherein the water content of said composition is <5% by weight of the total composition; and
   wherein the composition comprises particles the average size of which are <50 μm, and has the property of forming a dispersion when dissolved in a suitable solvent.

2. The composition of claim 1, wherein the composition has been freeze-dried to obtain the desired water content.

3. The composition of claim 1, wherein the composition has been evaporated to obtain the desired water content.

4. The composition of claim 1, comprising as alkali sodium or potassium soda ($Na_2CO_3$, $K_2CO_3$), silicates and optionally a hydroxide.

5. The composition according to claim 4, wherein the silicates are sodium or potassium silicate and the hydroxide is sodium or potassium hydroxide.

6. A solution of the composition as claimed in claim 1, wherein the solvent is selected from the group consisting of water and di-methyl-sulphoxide (DMSO).

7. A frozen solution of the composition as claimed in claim 1, wherein the solvent is selected from the group consisting of water and di-methyl-sulphoxide (DMSO).

8. A frozen solution of the composition as claimed in claim 1, wherein the complexing agent is selected from the group consisting of sodium acetate, tetra-sodium pyrophosphate, penta-sodium triphosphate, sodium hexametaphosphate and combinations thereof.

9. A method of analyzing foodstuffs, comprising
   calibrating an analysis apparatus or controlling said apparatus for reproducibility by performing a measurement on a standard sample, prepared by dissolving a standard sample composition as claimed in claim 1 in a suitable solvent;
   preparing a sample of the foodstuff of interest by comminuting said sample together with a dissolution aid comprising a complexing agent and an alkali salt to form a dispersion of the foodstuff; and
   performing an analysis on the sample using the calibrated apparatus.

10. The composition according to claim 1, wherein the water content is <1% by weight of the total composition.

11. The composition according to claim 1, wherein the water content is <0.1% by weight of the total composition.

12. The composition according to claim 1, wherein the particle size is <10 μm.

13. The composition according to claim 1, wherein the dispersion is dissolved in within 10 seconds.

14. A method of manufacturing a standard sample composition for foodstuff analysis, comprising mixing a complexing agent and an alkali salt;

dissolving the mixture in a solvent;

adding a known amount of a foodstuff cut into suitably large pieces, the water content of which in a native state is accurately known;

comminuting the obtained mixture to a particle size that forms a dispersion in solution, the average size of the particles being <50 μm and has the property of forming a dispersion when dissolved in a suitable solvent; and removing the solvent from the dispersion such that the solvent content is <5% by weight of the total composition.

15. The method according to claim 14, wherein the solvent is a polar solvent.

16. The method according to claim 15, wherein the solvent is water or di-methyl-sulphoxide.

17. The method according to claim 14, wherein the solvent content is <1% by weight of the total composition.

18. The method according to claim 14, wherein the solvent content is <0.1% by weight of the total composition.

19. The method according to claim 14, wherein the particle size is <10 μm.

20. The method according to claim 14, wherein the dispersion is dissolved in within 10 seconds.

* * * * *